United States Patent
Cameron et al.

(10) Patent No.: US 8,081,307 B2
(45) Date of Patent: *Dec. 20, 2011

(54) SYSTEMS AND METHODS FOR THE INSPECTION OF STENTS

(75) Inventors: Ian Cameron, Petersburg (CA); Andrew David Coppin Maw, Cambridge (CA); Hong Zhang, Kanata (CA); Calden Wloka, Toronto (CA); Sidney Watterodt, Cambridge (CA); Sang joon Park, Waterloo (CA); Anthony S. Andreacchi, San Jose, CA (US); Yung-Ming Chen, Cupertino, CA (US); Arnoldo M. Currlin, San Diego, CA (US); Antonio Garcia, San Jose, CA (US); Jason Van Sciver, Los Gatos, CA (US); Bryan D. Glenn, Murrieta, CA (US)

(73) Assignees: Abbott Cardiovascular Systems Inc., Santa Clara, CA (US); ATS Automation Tooling Systems Inc., Cambridge (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/888,337

(22) Filed: Sep. 22, 2010

(65) Prior Publication Data

US 2011/0007147 A1 Jan. 13, 2011

Related U.S. Application Data

(63) Continuation of application No. 11/764,009, filed on Jun. 15, 2007, now Pat. No. 7,812,941.

(51) Int. Cl.
*G01N 21/00* (2006.01)

(52) U.S. Cl. .................................. 356/237.1; 382/141
(58) Field of Classification Search .... 356/237.1–237.5, 356/241.1, 630–632, 625; 382/141, 152
See application file for complete search history.

(56) References Cited

U.S. PATENT DOCUMENTS

| | | | | |
|---|---|---|---|---|
| 4,162,126 A | * | 7/1979 | Nakagawa et al. | |
| 4,226,539 A | * | 10/1980 | Nakagawa et al. | |
| 4,410,278 A | * | 10/1983 | Makihira et al. | |
| 5,012,117 A | * | 4/1991 | Karafa et al. | |
| 5,186,887 A | * | 2/1993 | Yaginuma | |
| 5,422,743 A | * | 6/1995 | Farrell et al. | |
| 5,602,646 A | * | 2/1997 | Bernardin et al. | |
| 5,897,911 A | | 4/1999 | Loeffler | |

(Continued)

FOREIGN PATENT DOCUMENTS

DE 100 32 398 2/2001
(Continued)

OTHER PUBLICATIONS

U.S. Appl. No. 10/750,312, filed Dec. 30, 2003, Desnoyer et al.

(Continued)

*Primary Examiner* — Hoa Pham
(74) *Attorney, Agent, or Firm* — Squire, Sanders & Dempsey (US) LLP

(57) ABSTRACT

A system and method for inspecting stents can involve an inspection camera to take an image of the stent and a computer system for analyzing the image to determine the presence of any coating defects. The determination can be made by masking out a portion of the stent, identifying deviations from a strut edge, and/or highlighting features protruding from a stent external boundary defining an outer diameter. The image can be taken after a focus feedback camera determines the position of the stent.

10 Claims, 18 Drawing Sheets

U.S. PATENT DOCUMENTS

| | | | |
|---|---|---|---|
| 6,527,863 | B1 | 3/2003 | Pacetti et al. |
| 6,606,403 | B2 * | 8/2003 | Freifeld |
| 7,048,962 | B2 * | 5/2006 | Shekalim et al. |
| 7,162,073 | B1 * | 1/2007 | Akgul et al. .................. 382/149 |
| 7,208,190 | B2 | 4/2007 | Verlee et al. |
| 7,402,329 | B2 | 7/2008 | Pacetti et al. |
| 7,404,979 | B1 | 7/2008 | Pacetti |
| 7,505,124 | B2 * | 3/2009 | Kreckel et al. |
| 7,735,449 | B1 | 6/2010 | Harold et al. |
| 7,776,381 | B1 | 8/2010 | Tang et al. |
| 2005/0119720 | A1 | 6/2005 | Gale et al. |
| 2006/0035012 | A1 | 2/2006 | Pacetti et al. |
| 2007/0003688 | A1 | 1/2007 | Chen et al. |
| 2007/0073134 | A1 * | 3/2007 | Teichman et al. |
| 2007/0219615 | A1 * | 9/2007 | Freifeld et al. |
| 2007/0259100 | A1 | 11/2007 | Guerriero et al. |
| 2008/0037031 | A1 * | 2/2008 | Cole et al. |
| 2008/0042662 | A1 | 2/2008 | Abraham |
| 2008/0087474 | A1 | 4/2008 | Nufer et al. |
| 2008/0307668 | A1 | 12/2008 | Watterodt |
| 2008/0311281 | A1 | 12/2008 | Andreacchi |
| 2008/0312869 | A1 | 12/2008 | Hemphill |

FOREIGN PATENT DOCUMENTS

| | | |
|---|---|---|
| EP | 1 195 584 | 4/2002 |
| WO | WO 2007/130257 | 11/2007 |

OTHER PUBLICATIONS

U.S. Appl. No. 10/805,047, filed Mar. 18, 2004, Yip et al.

Invitation to pay additional fees, including communication relating to the results of the partial international search, for PCT/US2008/061806, mailed Aug. 27, 2008, 9 pgs.

International Search Report and the Written Opinion, for PCT/US2008/061806, mailed Dec. 5, 2008, 19 pgs.

* cited by examiner

SYSTEMS AND METHODS FOR THE INSPECTION OF STENTS

CROSS-REFERENCE TO RELATED APPLICATION

This is a continuation of application Ser. No. 11/764,009, filed Jun. 15, 2007 now U.S. Pat. No. 7,812,941, the entire disclosure of which is incorporated herein by reference.

DESCRIPTION OF THE INVENTION

1. Field of the Invention

The present invention relates to systems and methods for the inspection of stents.

2. Background of the Invention

Manufactured cylinders are employed in a number of applications. One such application is the use of stents in the treatment of cardiovascular conditions. Stents are generally small, hollow cylinders formed from a metal lattice structure that may be inserted into an artery to hold it open and allow blood to flow. Stents may be manufactured with a variety of dimensions depending on their application. Stents may also be coated with drugs in order to aid in the treatment of a disease or condition.

The ability to quickly and accurately inspect stents and other cylinders for defects is an important part of the process of manufacturing such devices. In some applications, the required tolerances and/or regulations may be extremely demanding. Additionally, the small dimension of some cylinders (such as stents) can make visual inspection extremely challenging and time consuming. Furthermore, in addition to manufacturing defects, drug coating on stents introduces the possibility for other defects. For example, the coating may pool between gaps in the lattice structure, or may allow a foreign object (such as dust or a polymer strand) to adhere to the stent. The embodiments of the present invention address these as well as other needs.

BRIEF SUMMARY OF THE INVENTION

In aspects of the present invention, a method for inspecting a stent comprises creating at least one image of at least a portion of the stent, and analyzing the image to inspect the stent for defects, the analyzing comprising masking out a strut of the stent in the image, and identifying a defect associated with a feature remaining in the image after the masking out of the strut.

In aspects of the present invention, a system for inspecting a stent comprises a camera for creating an image of at least a portion of the stent. The system further comprises a computer system for controlling the camera and analyze for analyzing the image to inspect the stent for defects, the computer system configured to mask out of the image a strut of the stent, and identify a defect associated with a feature remaining in the image after the strut is masked out.

In aspects of the present invention a method for inspecting a stent comprises determining a position of the stent using a focus feedback camera, and focusing an inspection camera on the stent based on the position of the stent determined from the focus feedback camera. The method further comprises creating an image of at least a portion the stent using the inspection camera, wherein the stent is at least partially disposed between a light source and the inspection camera. The method further comprises analyzing the image to inspect the stent for a defect.

In aspects of the present invention, a system for inspecting a stent comprises a light source for illuminating the stent, an inspection camera for creating an image of at least a portion of the stent, a computer system for controlling the inspection camera and for analyzing the image to identify a defect, and a focus feedback camera controlled by the computer system, the focus feedback camera configured to measure a position of the stent. The inspection camera is configured to focus on the stent based on the position of the stent measured by the focus feedback camera.

BRIEF DESCRIPTION OF THE DRAWINGS

A more complete understanding of the present invention may be derived by referring to the detailed description and claims when considered in connection with the following illustrative figures. Wherever possible, the same reference numbers will be used throughout the drawings to refer to the same or like features.

Elements in the figures are illustrated for simplicity and clarity and have not necessarily been drawn to scale. For example, the dimensions of some of the elements in the fig-

DETAILED DESCRIPTION OF EXEMPLARY EMBODIMENTS

The systems and methods introduced herein summarize exemplary embodiments of the present invention. Embodiments of the present invention may be described herein in terms of various functional blocks and processing steps. Such functional blocks may be realized by any number of hardware and/or software components configured to perform specified functions and achieve various results. For example, embodiments of the present invention may employ any desired material, machine, processor and/or integrated circuit component, interface, transmission media, integrated and/or distributed computer system, storage system, database, and the like, which may carry out any desired function under the control of one or more computers and/or other control devices. Additionally, the present invention may employ any number of conventional techniques for manufacturing, robotic manipulation, data storage and analysis, component interfacing, data processing, information conversion, communication, and the like. Furthermore, the present invention may be practiced in conjunction with any number of processes, systems, and/or devices.

Figure 1:
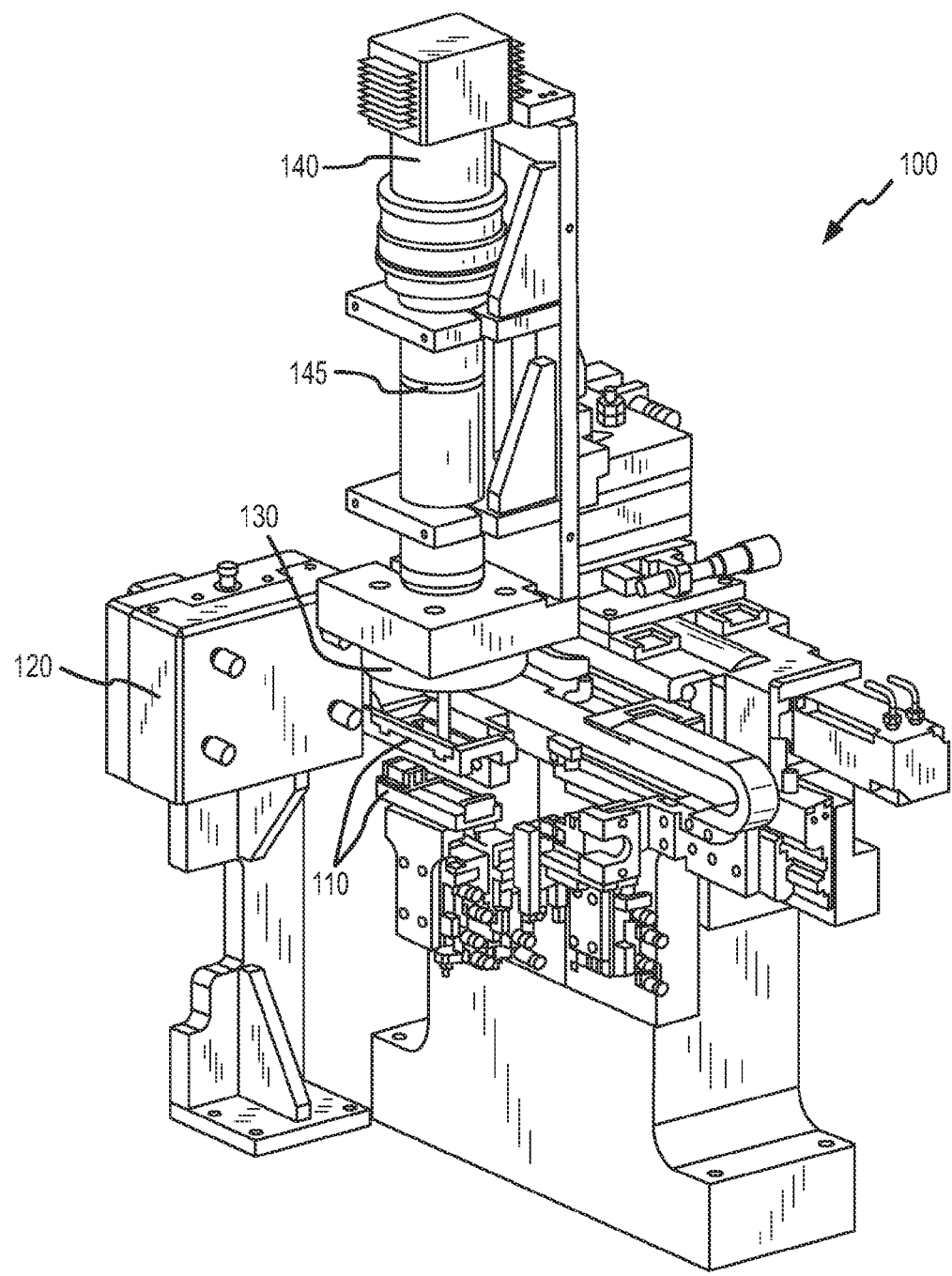
FIG. 1 is a three-dimensional design schematic depicting an exemplary system for inspecting a stent according to various aspects of the present invention.
Figure 2:
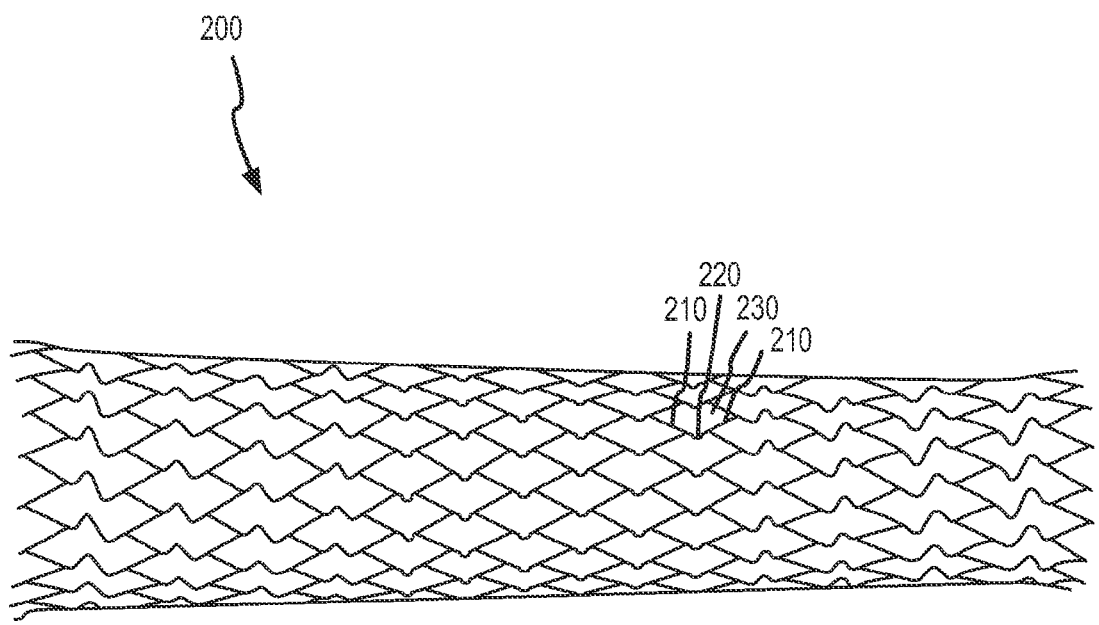
FIG. 2 is a side view of an exemplary stent.

Referring to FIG. 1, an inspection system 100 may be configured to inspect cylinders to determine whether proper manufacturing tolerances have been met, as well as to identify defects. The inspection system 100 may be configured to inspect any sort of cylinder of any dimension and configuration in order to achieve any desired result. For example, an inspection system 100 according to various aspects of the present invention may be configured to inspect a stent 200 as depicted in FIG. 2. The exemplary stent 200 in FIG. 2 is formed from a plurality of struts 210. The struts 210 are radially expandable (e.g., balloon expandable or self-expandable) and interconnected by connecting elements or links 220 that are disposed between adjacent struts 210, leaving lateral openings or gaps 230 between adjacent struts 210. The struts 210 and the connecting elements 220 define a hollow cylindrical body. The inspection system 100 may include a roller assembly 110, a drive system 120, a light 130, and a camera 140. The inspection system 100 may interface with any other appropriate systems and devices, such as a computer control system.

Figure 3:
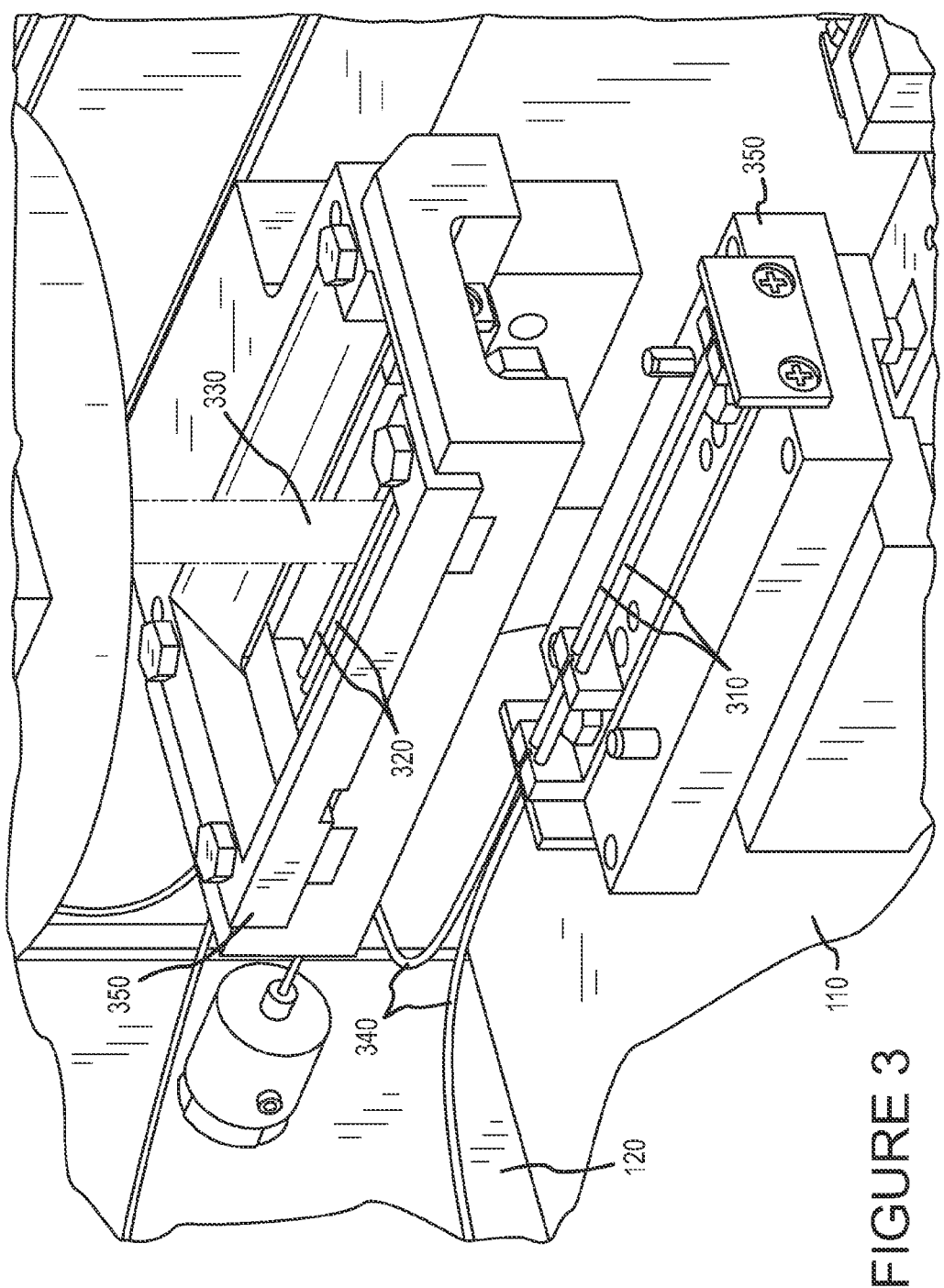
FIGS. 3 and 4 are three-dimensional design schematics depicting details of the system in FIG. 1.

The roller assembly 110 holds the stent 200 in place and rotates the stent 200 about its longitudinal axis to allow the stent 200 to be imaged. The roller assembly 110 may be configured to handle any cylinder of any configuration and dimension. Referring now to FIG. 3, a roller assembly 110 according to various aspects of the present invention may include a lower pair of rollers 310 and an upper pair of rollers 320. The roller assembly 110 may be configured to allow the upper rollers 320 to rise to allow a stent 200 to be placed between the two lower rollers 310, then drop down to cradle the stent 200 between the four rollers 310, 320. Similarly, the lower rollers 310 may be configured to drop down to allow the loading and unloading of the stent 200, then rise up to allow the stent 200 to be cradled by the four rollers 310, 320. The rollers 310, 320 may interface with any suitable structure or device. For example, the rollers 310, 320 may be supported by bearing blocks 350 that may be configured to move up and down to allow loading and unloading of the stent 200. The rollers 310, 320 may be configured to move in any direction and in any manner to achieve any other desired result.

Figure 4:
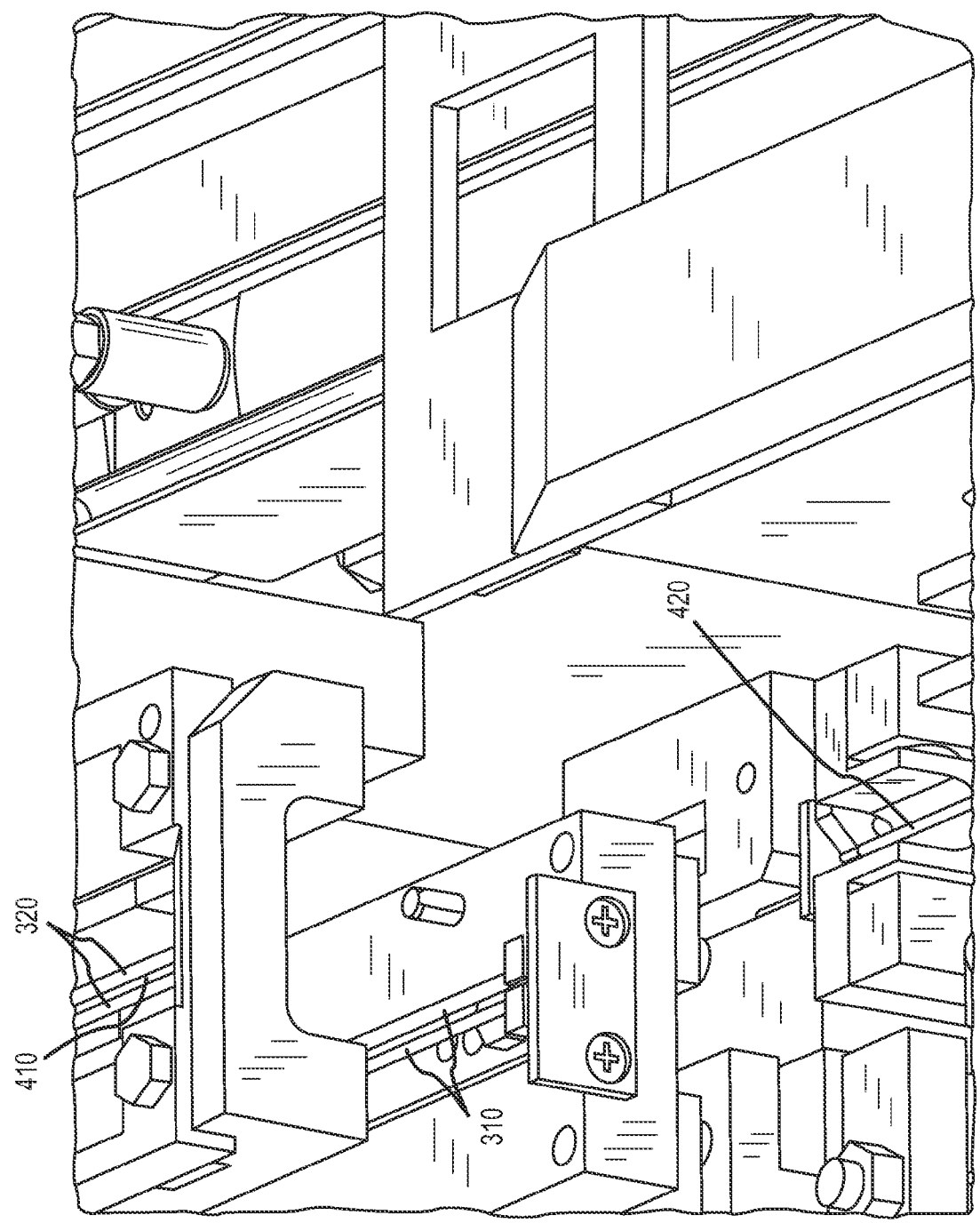

The rollers 310, 320 may be of any suitable dimension, and may be positioned in any manner. For example, referring to FIGS. 3 and 4, the roller pairs 310, 320 may be of suitable length and width to hold a stent 200 for imaging, and may include a gap 410 between two pairs of rollers 310, 320 to allow a camera 140 to view the stent 200. As depicted in FIGS. 3 and 4, the camera's 140 field of view 330 passes between the gap 410 between the two top rollers 320 to view a stent 200 held by the roller assembly 110.

The rollers 310, 320 are configured to avoid damaging the stent 200 while providing a stable surface to rotate the stent 200 upon. The rollers 310, 320 may comprise any suitable material and may include any structural property. For example, the rollers 310, 320 may comprise a rubberized coating to allow the stent 200 to be cradled between the rollers 310, 320 without deforming or compressing the stent 200, and/or without damaging a drug coated on the stent 200 and/or the structure of the stent 200. Those skilled in the art will recognize that aspects of the present invention may be practiced with minor deformations of the stent 200 that do not significantly affect the structure of the stent 200 or any coating thereon. Furthermore, the rollers 310, 320 may be configured to rigidly support the stent 200 and rotate without distorting, which could cause the rollers 310, 320 to slip against the surface of the stent 200. The rollers 310, 320 may interface with any suitable system or device, such as a drive system 120.

The roller assembly 110 may be connected to a drive system 120 configured to cause the rollers 310, 320 to rotate. The drive system 120 may comprise any suitable number of systems and/or devices to control the rotation of the rollers. In one embodiment of the present invention, for example, the drive system 120 may comprise a set of four electric motors that are independently controlled by software operating on a computer system, with each electric motor controlling a separate roller. The drive system 120 may be configured in any manner to achieve any suitable result, such as to rotate the rollers 310, 320 in a synchronous manner, and/or to rotate one or more rollers 310, 320 independently from each other. The drive system 120 may rotate the rollers 310, 320 in any direction, for any duration, and at any appropriate speed. The drive system 120 may be controlled by the computer system to rotate the stent 200 a predetermined amount in order to image different portions of the stent 200 with the camera 140. The drive system 120 may be controlled by a computer system that interfaces with the camera 140 and/or any other component of the inspection system 100, allowing the computer system to coordinate the rotation of the stent 200 with the imaging of the stent 200.

The drive system 120 may be connected to the roller assembly 110 in any suitable manner, such as through flexible drive shafts 340 configured to move with the roller pairs 310, 320 to allow the stent 200 to be loaded and unloaded from the roller assembly 110. The flexible drive shafts 340 may comprise any suitable material and may be of any appropriate dimension. The flexible drive shafts 340 may be configured to dissipate ancillary forces that may otherwise be transferred from the drive system 120, causing the rollers 310, 320 to distort.

Figure 5:
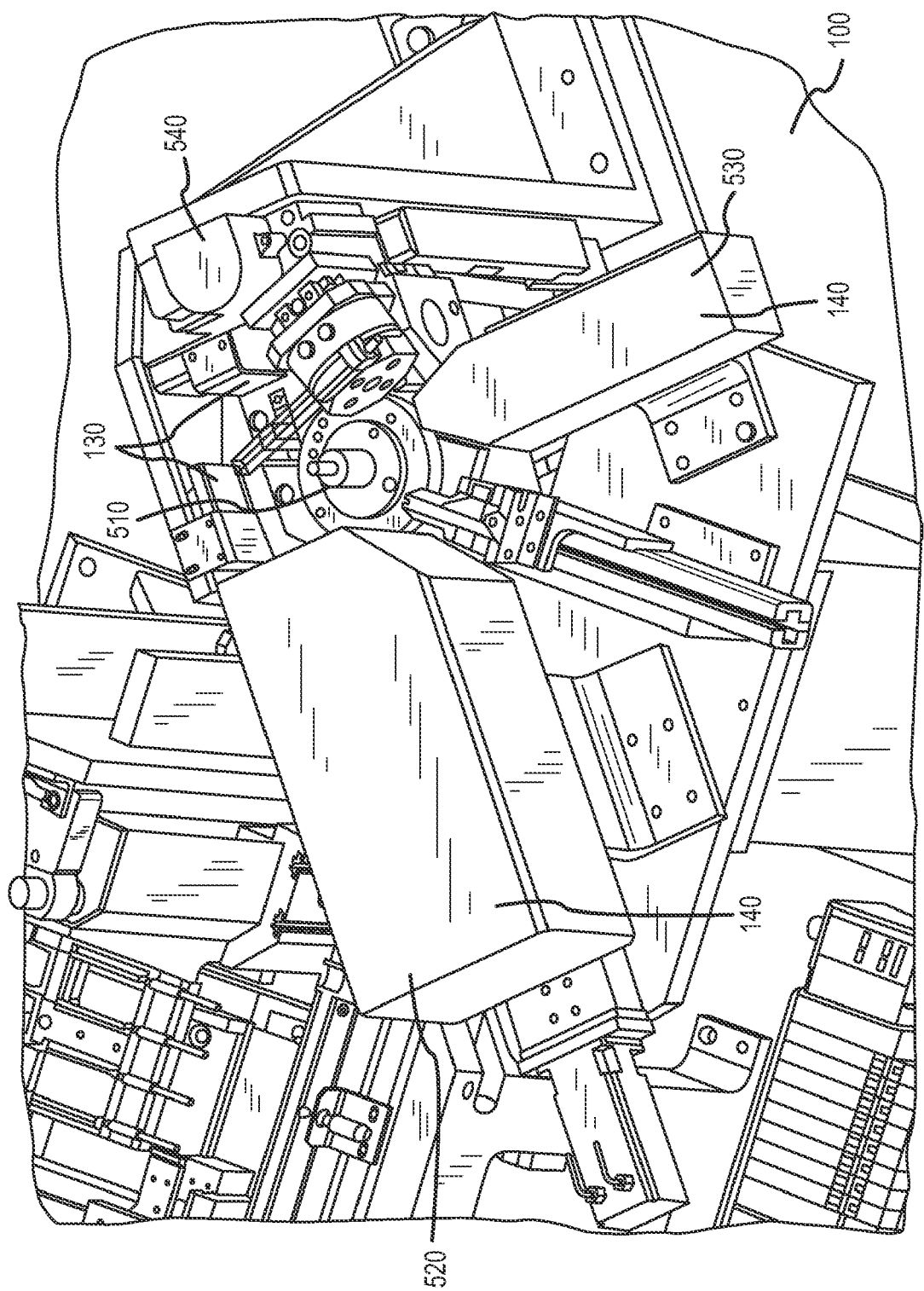
FIG. 5 is a three-dimensional design schematic depicting an exemplary system for inspecting a stent according to various aspects of the present invention.
Figure 6:
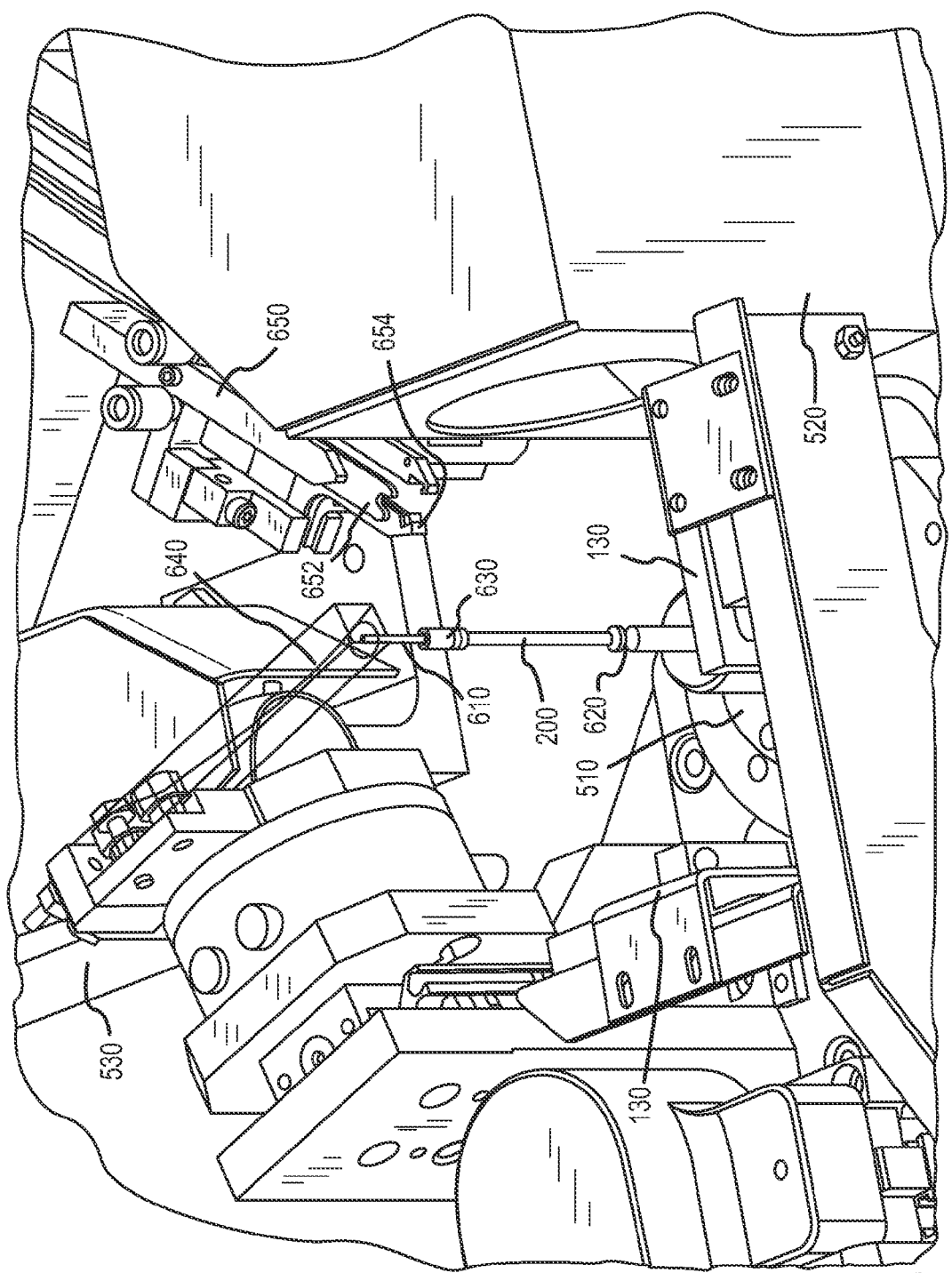
FIG. 6 is a three-dimensional design schematic depicting details of the system in FIG. 5.

The stent 200 may be held in place in any appropriate manner to achieve any desired result. In one embodiment of the present invention as shown in FIG. 5, for example, the stent 200 may be held by a rotating base 510 to allow defects protruding from the stent 200 to be detected. The base 510 holds the stent 200 in the field of view of two cameras 520, 530. The base 510 may be raised and lowered using a positioning system 540 to allow the cameras 520, 530 to image the full length of the stent 200. The stent 200 is located between the cameras 520, 530 and light sources 130 that illuminate the boundary edges of the stent 200. As depicted in FIG. 6, the base 510 may hold the stent 200 in place using a mandrel 610 connected to a bottom collet 620. In this exemplary embodiment of the present invention, the mandrel 610 is placed through the interior of the stent 200 and a top collet 630 is brought down to capture the stent 200 concentrically around the mandrel 610 by a capture arm 640. The capture arm 640 may also aid in holding the stent 200 and mandrel 610 as the base 510 rotates.

The mandrel 610 may interface with the stent 200 in any suitable manner. For example, the mandrel 610 may be configured to pass through the stent 200 without contacting its interior so as to avoid damaging the structure of the stent 200 and/or a drug coating the stent 200. The mandrel 610 may releasably connect to the top and bottom collets 620, 630 to aid in the transfer of the stent 200 to and from the base 510.

The top and bottom collets 620, 630 engage the stent 200 to hold it in place while it is rotated by the base 510 and imaged by the cameras 520, 530. The collets 620, 630 may engage the stent 200 in any suitable manner, such as by inserting a tapered and/or conical end of the collet 620, 630 into the interior of the stent 200 at each end of the stent 200. The base 510 may rotate the stent 200 in any direction, at any speed, and for any duration. For example, the base 510 may rotate the stent 200 in 5-degree increments to allow defects protruding from the stent 200 to be imaged by the cameras 520, 530.

Figure 7A:
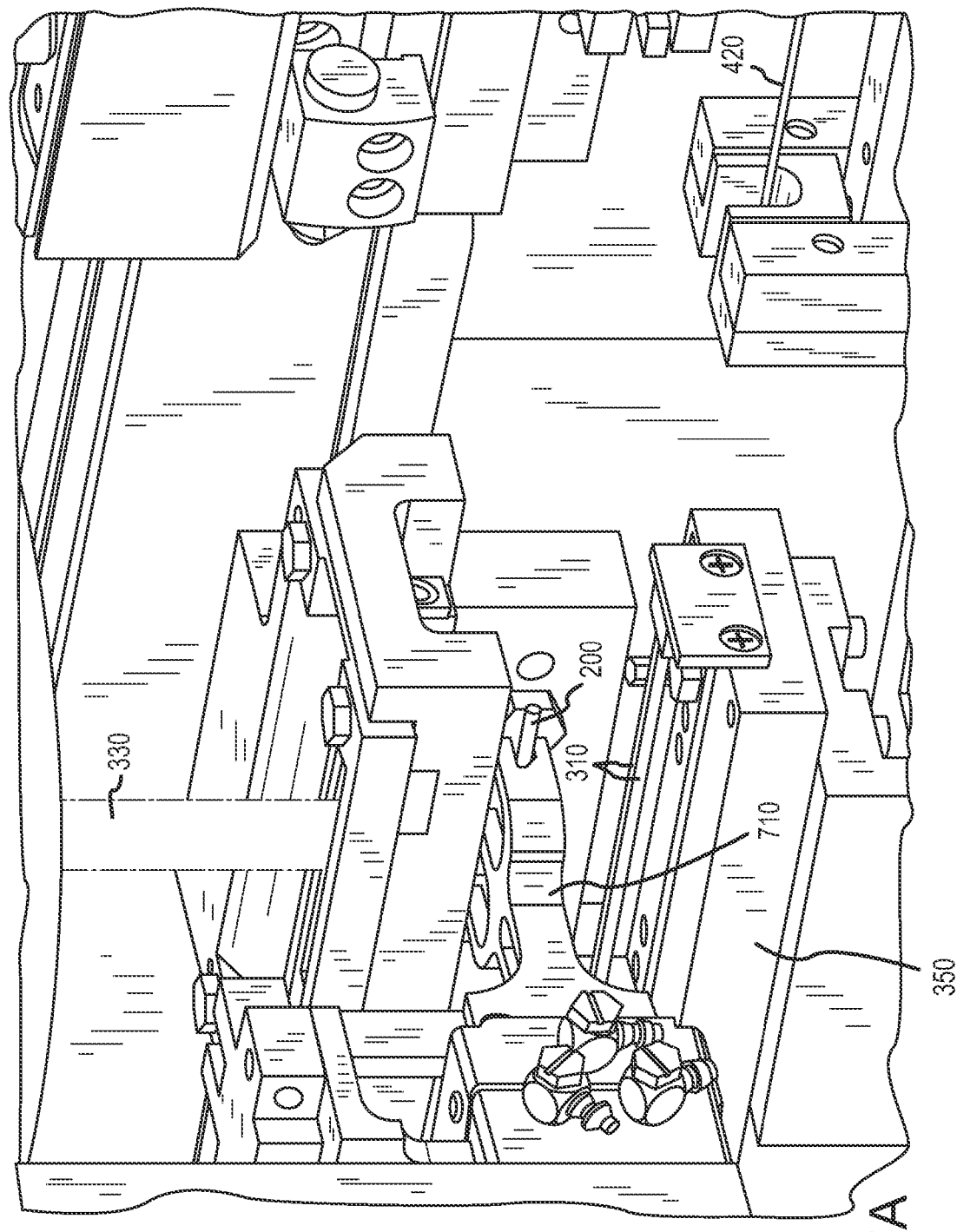
FIG. 7A is a three-dimensional design schematic depicting details of a system for stent inspection according to various aspects of the present invention.

The stent 200 may be handled and moved by one or more robotic devices in order to automate the process of inspecting the stent 200. The stent 200 may be manipulated in any suitable manner by any appropriate device or system. For example, referring to FIG. 7A, the stent 200 may be moved to and from the roller assembly 110 by a transfer arm 710. The transfer arm 710 may be configured to transfer the stent 200 to other systems and devices, such as other inspection stations. The transfer arm 710 may be controlled in any manner, such as through software operating on a computer system. Any number of transfer arms 710 may be employed in an inspection system 100, each having any suitable configuration to manipulate and move the stent 200.

Other robotic devices may be employed to automate the inspection of cylinders in an inspection system 100. In the exemplary embodiment of the present invention shown in FIG. 6, a stent 200 may be provided to the base 510 by a robotic transfer arm 710, and a capture arm 640 may engage the top collet 630 with the top of the stent 200. The capture arm 640 may hold the collet 630 in place to help keep the stent 200 from deforming or otherwise moving on the base 510 as it rotates.

Additionally, a stabilizer arm 650 may be used to automatically position the stent 200 on the base 510. In the exemplary embodiment of the present invention depicted in FIG. 6, a stabilizer arm 650 may comprise a collet interface 652 and a set of jaws 654. The stabilizer arm 650 may be configured to pick the stent 200 up with the jaws 654 while the stent 200 is on the base 510 and maneuver the stent 200 such that the stent 200 properly interfaces with the bottom collet 620. For example, in the case where a bottom collet 620 comprises a conical surface that engages with the interior of the stent 200 at one end, the stabilizer arm 650 may pick up the stent 200 and drop it over the conical surface of the bottom collet 620 such that the stent 200 properly settles over the bottom collet 620. Similarly, the collet interface 652 may be configured to engage the top collet 630, such as by interfacing with a groove in the top collet 630. The collet interface 652 may lift the top collet 630 up and down to allow a conical surface to engage inside the stent 200. The stabilizer arm 650 may comprise any other suitable structures and devices for manipulating the positioning of a cylinder.

Figure 7B:
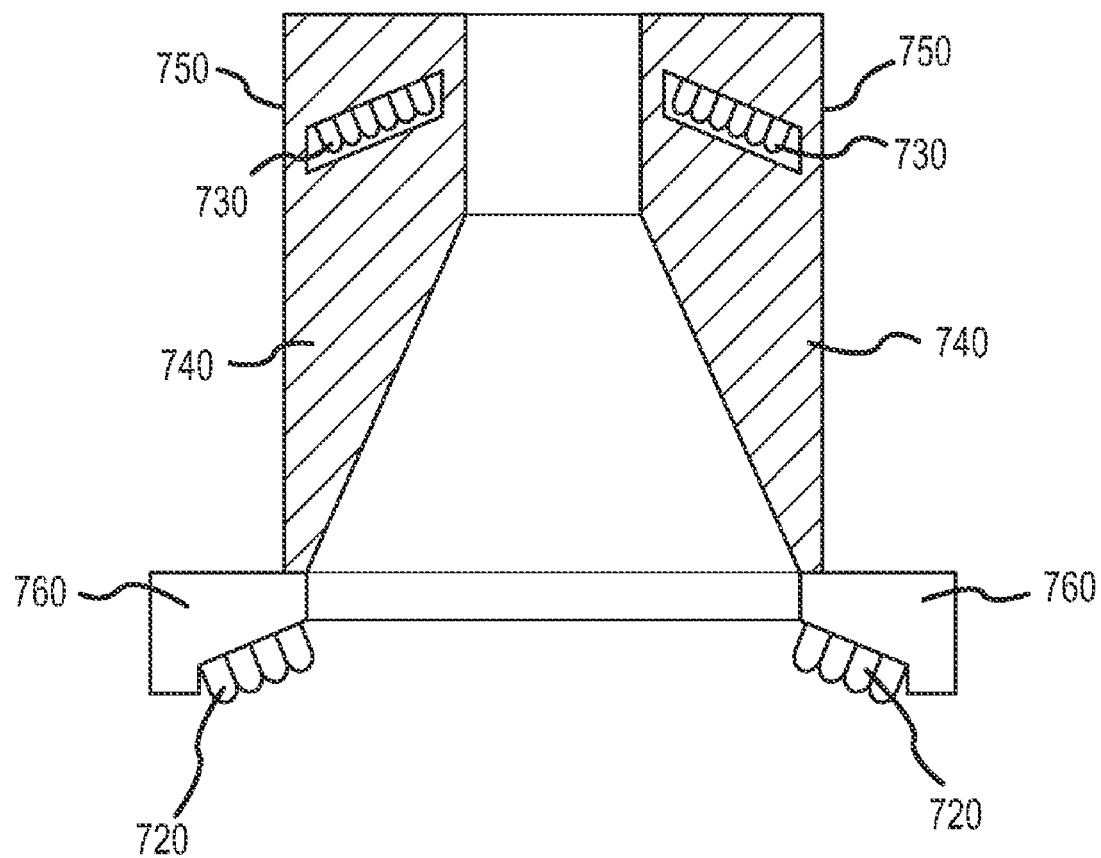
FIG. 7B is a side view of an exemplary light source according to various aspects of the present invention.

The inspection system 100 includes a light source 130 configured to illuminate a cylinder for inspection. The light source 130 may comprise any suitable number of devices and may have any appropriate structure. For example, referring to FIG. 7B, an exemplary light source 130 according to various aspects of the present invention may comprise a ring light 720 concentrically placed around a dome light 730. Any desired configuration of ring light and dome light may be used in conjunction with the present invention, such as an LDR2-90 ring light and an LDM-50 dome light, both from CCS, Inc. In this exemplary embodiment of the present invention, the ring light 720 may surround the stent 200 to provide light to the stent 200 at steep angles, i.e.—nearly parallel to the stent 200, in order to create shadows on the surface of the stent 200 to allow a camera 140 viewing the stent 200 to detect surface imperfections of the stent 200. The ring light 720 may be supported by a light can 760. The dome light 730 may be employed to provide lighting to portions of the stent 200 that otherwise would be left dark by the ring light 720. The dome light 730 may be supported by a light can 750 that includes a translucent material 740 to provide diffuse light from the dome light 730 to the cylinder being inspected. In another exemplary embodiment, referring now to FIG. 5, the light sources 130 may comprise substantially rectangular lights to provide backlighting for an inspection camera 520 and a focus feedback camera 530.

The light source 130 may comprise any other appropriate systems and devices, such as a light source positioning system configured to adjust the position of various elements of the light source 130 to illuminate the stent 200 from various angles relative to the camera 140. For example, the light source positioning system may be configured to allow the dome light 730 to be positioned independently of the ring light 720. The ring light 720 and dome light 730 may be oriented in any appropriate manner to achieve any result. For example, the dome light 730 may be positioned within the ring light 720 to allow the camera 140 to view the stent 200 between a gap between the ring light 720 and dome light 730.

The light source 130 may provide lighting having any desired characteristics, such as wavelength, intensity, and the like. For example, the light source 130 may be configured to provide lighting that is diffuse, that is, light that scatters over a large angular range, in order to avoid glare and/or non-uniform areas of brightness to be viewed by the camera 140 as well as to compensate for a tendency of non-uniform and highly-reflective surfaces on a cylinder to scatter light away from the camera 140. Additionally, the light source 130 may provide light in a specific spectrum in order to avoid affecting a drug or other substance coating a stent 200. In one exemplary embodiment of the present invention, the light source 130 may be configured to provide lighting having a wavelength of about 600 nm to about 700 nm in order to avoid activating a drug coating the stent 200.

The light source 130 may interface with any suitable system, and device to achieve any desired purpose. For example, the light source 130 may be in communication with a computer system configured to control the intensity, wavelength, and position of the light source 130. Any characteristic of the lighting provided by elements of the light source 130, such as wavelength, intensity, and the like, may be controlled individually or in concert with other elements as appropriate. For example, in one exemplary embodiment of the present invention, the ring light 720 and dome light 730 may be independently turned off or on. The ring light 720 may be turned off and the dome light 730 turned on in order to aid in the inspection of the interior of a stent 200. Alternatively, the ring light 720 may be turned on and the dome light 730 turned off in order to aid in the inspection the roughness of the surface of a stent 200 or other cylinder.

The light source 130 may interact with any structure in the inspection system 100 in any appropriate manner. For example, the light source may utilize the structure of the bearing blocks 350 holding the rollers 310, 320 to help contain the illumination provided by the light source 130 and/or to prevent external light from interfering with the imaging of a cylinder. The light source 130 may be positioned in any manner, such as between the camera 140 and the stent 200 as described previously. Alternatively, referring now to FIG. 5, an inspection system 100 according to various aspects of the present invention may be configured such that the stent 200 is between a light source 130 and an inspection camera 520, and between another light source 130 and an focus feedback camera 530.

The camera 140 takes an image of a portion of a cylinder for analysis. Any appropriate type of camera 140 may be utilized in an inspection system 100. In one exemplary embodiment of the present invention, the camera 140 may comprise a linescan camera 140 configured to image a single row of pixels at a time. A linescan camera 140 having any appropriate characteristics may be utilized, such as a Dalsa digital line scan camera with a 1×6000 aperture. The camera 140 may image any part of the stent 200, as well as any features and/or defects protruding from the stent 200. Additionally, the camera 140 may image features such as apertures in the surface of a stent 200. Any other portion and feature of a cylinder may be imaged as well. For example, the interior of a stent 200 or other hollow cylinder having apertures in its surface may be imaged by the inspection system 100 by moving the camera close to the stent 200, allowing the camera 140 to focus beyond the apertures to view the interior. The camera 140 may be positioned at any suitable distance to allow the camera 140 to focus on the interior of the stent 200. An image created by the camera 140 may be generated in any format and in any medium, such as a digitized image stored in the memory of a computer system.

Figure 8:
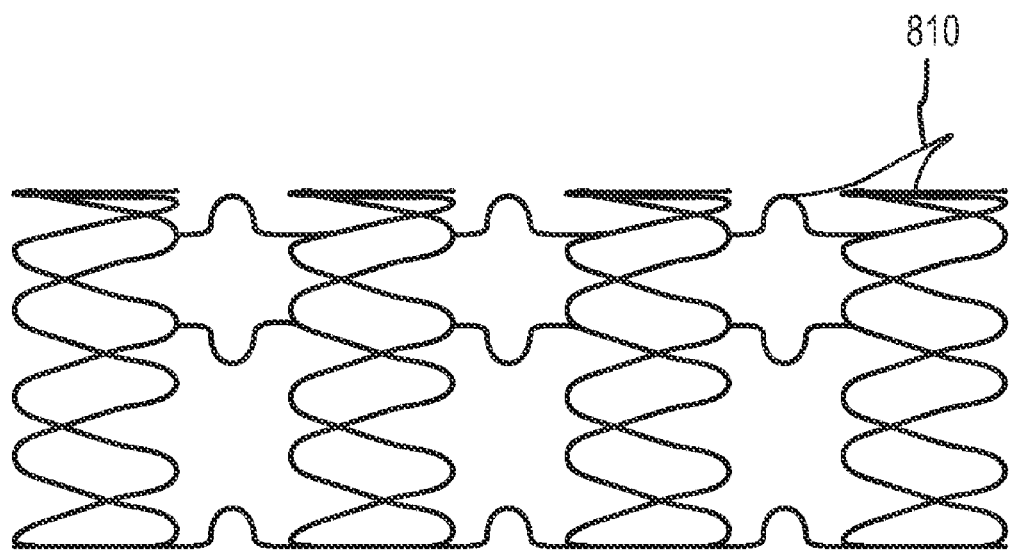
FIGS. 8 and 9 depict exemplary images of defects protruding from a stent.
Figure 9:
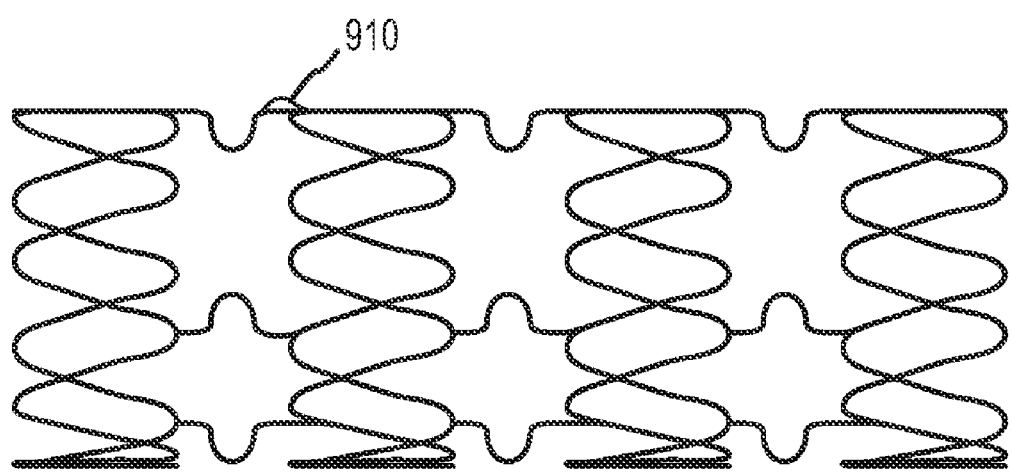

Any number of cameras 140 of any type may be employed in an inspection system 100. For example, referring to FIG. 5, an inspection system 100 according to various aspects of the present invention may comprise two field of view cameras 520, 530 positioned such that their facings are ninety degrees relative to each other. In this exemplary embodiment of the present invention, the inspection camera 520 captures an image of a stent 200 of a portion of the stent 200. The stent 200 is illuminated from behind by a light source 130, creating a backlight effect that highlights the external boundaries defining the width/diameter of the stent 200 structure as well as any features protruding from the external boundaries. For example, the image depicted in FIG. 8 indicates a defect 810 protruding from the stent 200. The inspection camera 520 may be configured to image the stent 200 at any resolution in order to inspect any feature of any dimension on a stent 200. Referring to FIG. 9, a protruding defect 910 may be identified even where the defect 910 is very small relative to the structure of the stent 200. For example, in some embodiments of the present invention, defects of ten micrometers or smaller can be identified.

The inspection camera 520 may create multiple images of the stent 200 in order to achieve any desired result. For example, the inspection camera 520 may create a plurality of images along the full length of a stent 200 that is otherwise longer than the field of view of the inspection camera 520. A positioning system 540 may be used to move the base 510 holding the stent 200 along the field of view of the inspection camera 520. The base 510 may rotate the stent 200 a predetermined amount, such as five degrees, to expose a new portion of the stent 200 to the inspection camera 520, and the imaging process can be repeated to image entire stent. The degree of rotation may be increased or decreased depending on the size of the defects sought to be identified and/or to increase the speed of the inspection process. By simultaneously imaging both edges defining the width of the stent 200 at each position of rotation, the stent 200 can be rotated only 180 degrees while still inspecting the full circumference of the stent 200.

An inspection system 100 may include a focus feedback camera 530 configured to detect any shifting of position by the stent 200 about the mandrel 610, particularly as the stent 200 is rotated. When the stent 200 shifts toward or away from the inspection camera 520, the stent 200 may move out of the focus of the inspection camera 520. The focus feedback camera 530 may be configured to detect a shift in position of the stent 200 and report the shift in position in order to cause the inspection camera 520 to be refocused. The focus feedback camera 530 may interact with any suitable system or device to identify and report a shift in position. For example, the focus feedback camera 530 may interface with a computer system that analyzes an image generated by the focus feedback camera 530, detects a shift in position of the stent 200, and causes the inspection camera 520 to refocus accordingly.

A camera 140 according to various aspects of the present invention may interact with any number of other systems and devices. For example, as shown in FIG. 1, a camera 140 may be utilized in conjunction with one or more lenses 145. A lens 145 may be configured in any manner to achieve any desired result, such as to allow the camera 140 to achieve a specific length of view to control the width of the linescan image being created. Similarly, the distance of one or more lenses 145 from the stent 200 may be selected to affect any appropriate characteristic of the image. For example, the lens 145 may be located closer to a stent 200 in order to create a higher-resolution image of a smaller portion of the stent 200, and farther away to create a lower-resolution image of a larger portion of the stent 200. Additionally, positioning the lens closer to a stent 200 may aid in preventing any movement of the stent from affecting the quality of the image.

A camera 140 may also operate in conjunction with a camera positioning device, for example to allow the camera 140 to be moved toward and away from the cylinder being inspected. Additionally, the camera positioning device may be configured to allow the camera 140 to be moved laterally, such as along the length of a cylinder that is too long to fit in the view of the camera 140 in a single image.

Referring to FIG. 4, an inspection system 100 may include a background mandrel 420. The background mandrel 420 may be inserted within the inner diameter of a stent 200 to provide a background for imaging by the camera 140. In order to prevent damage to the stent 200 or a coating on the stent 200, the background mandrel 420 may be configured to dispose within the stent 200 without touching the interior of the stent 200. For example, in the exemplary embodiment of the present invention depicted in FIG. 3, the roller assembly 110 fully supports and rotates the stent 200 to allow the background mandrel 420 to be disposed within the stent 200 without touching its interior.

An inspection system 100 according to various aspects of the present invention may be operated and controlled in any manner. For example, various systems and processes may be controlled by one or more software programs operating on one or more computer systems. The computer system may interface with any of the individual components of the inspection system 100, such as the roller assembly 110, light source 130, camera 140, etc., as well as any other systems and devices external to the inspection system 100. Any process implemented and/or controlled by the computer system may be operated manually, such as by a human operator or other control system, and/or configured to operate automatically, such as under the control of a software program.

The computer system may control any function and aspect of the inspection system 100 to achieve any desired result. For example, the computer system may control the rotation and positioning of a cylinder by the roller assembly 110 and/or base 140 during imaging. The computer system may also control one or more cameras 140 in taking an image of the cylinder, including moving and focusing the camera 140 to take images along the length of a stent 200 in order to image its full length. The computer system may use input from a focus feedback camera 530 to control the focusing of an inspection camera 520. The position, intensity, wavelength, and other characteristics of the light source 130 may be controlled by the computer system. The computer system may also control any features of the inspection system 100 for transferring and manipulating the stent 200, such as the wire capture arm 640, stabilizer arm 650, and transfer arm 710. The computer system may interface with any suitable sensing systems or devices to achieve any purpose, such as to detect the pressure exerted on a cylinder, measure the position of a stent 200 with relation to other features in the inspection system 100, and the like.

The computer system may be configured to process and/or analyze images of a cylinder. The computer system may be configured to perform any suitable analysis, such as to inspect a stent 200 for defects. The computer system may be configured to process images in any suitable manner. For example, the computer system may sequence and/or index images with reference to the position of the roller assembly 110 or base 140 when the image was taken so that the images can be related back to the part of the cylinder imaged.

Figure 10:
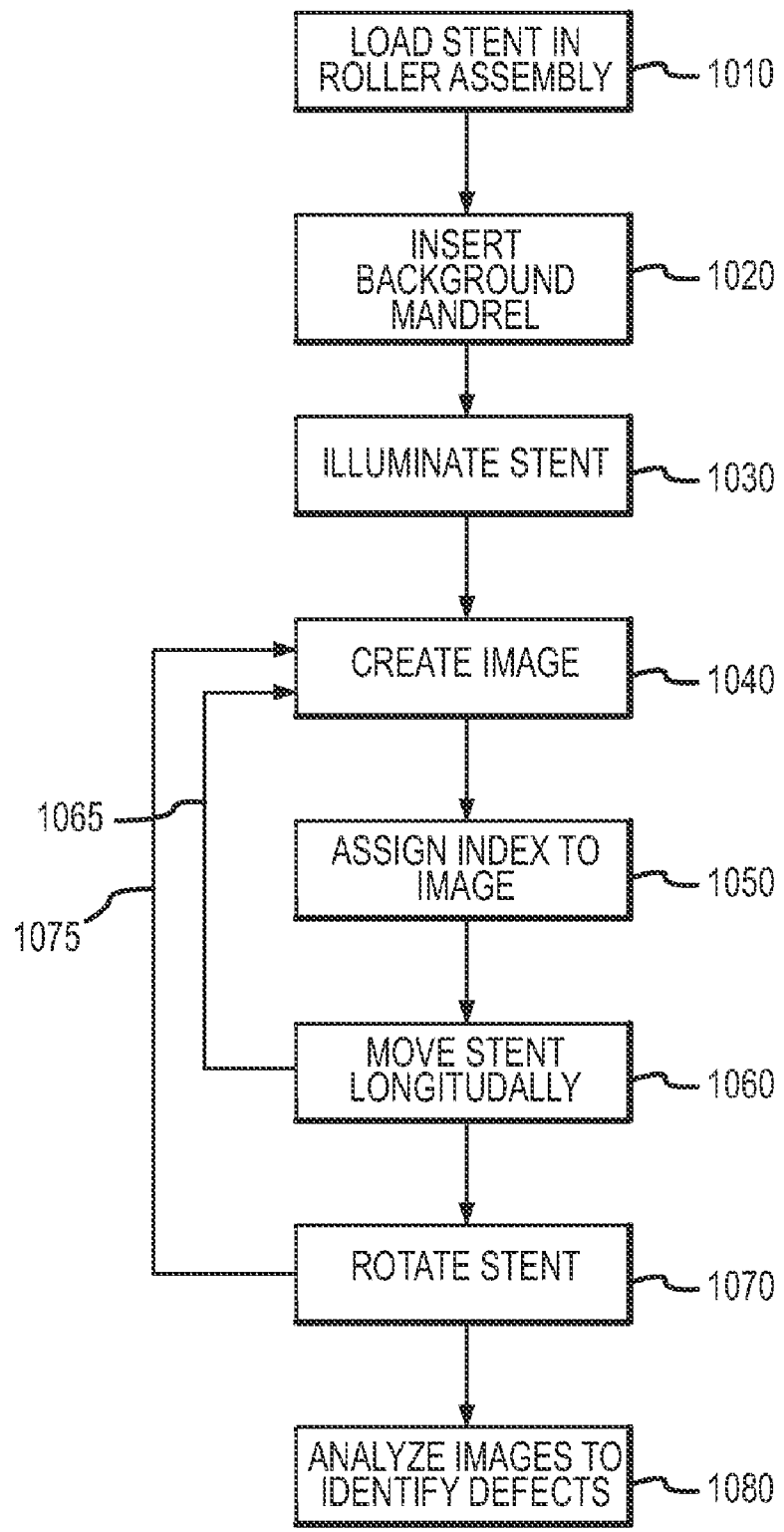
FIG. 10 is a process flow diagram illustrating an exemplary process for inspecting a stent according to various aspects of the present invention.

FIG. 10 illustrates an exemplary process that may be employed by an inspection system 100 for inspecting stent 200s according to various aspects of the present invention. A stent 200 is automatically provided to a roller assembly 110 by a transfer arm 710 (1010). A background mandrel 420 is inserted through the interior of the stent 200 to provide a background to for the image of the stent 200 (1020). The light source 130 illuminates the stent 200 (1030) and the linescan camera 140 creates an image of a portion of the stent 200 (1040), the image comprising a single row of pixels along a portion of the length of the stent 200. The images may be indexed to record their relation to the physical structure of the stent 200 (1050). If the length of the stent 200 is outside the field of view of the camera 140, the camera 140 and/or the stent 200 may be moved to allow the camera 140 to image the full length of the stent 200 (1060). This longitudinal movement may be repeated in order to allow the full length of the stent to be imaged (1065). The stent 200 is rotated by the roller assembly 110 to allow the next row of pixels to be imaged (1070) and the process is repeated (1075) until the entire stent 200 is imaged.

Figure 11:
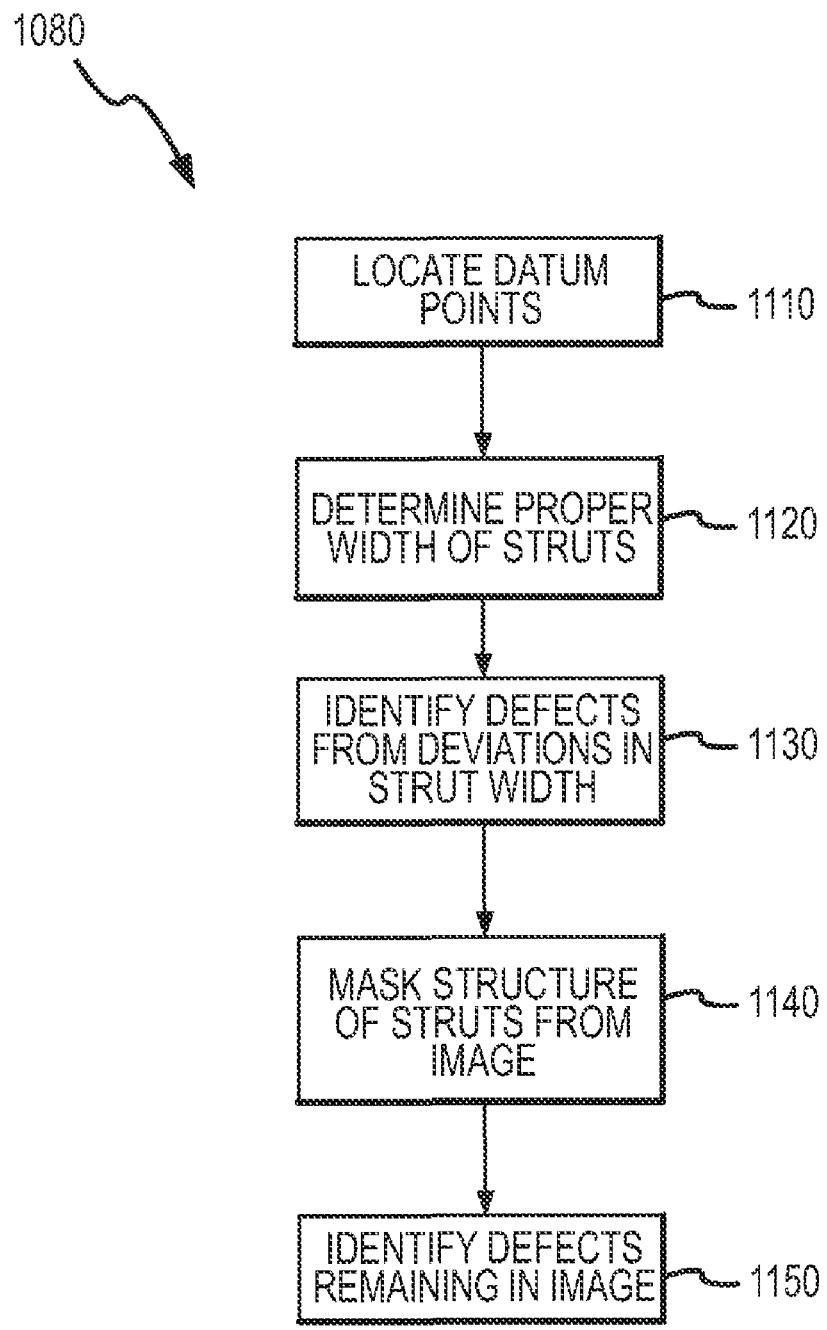
FIG. 11 is a process flow diagram illustrating an exemplary process for identifying defects associated with a stent according to various aspects of the present invention.
Figure 12:
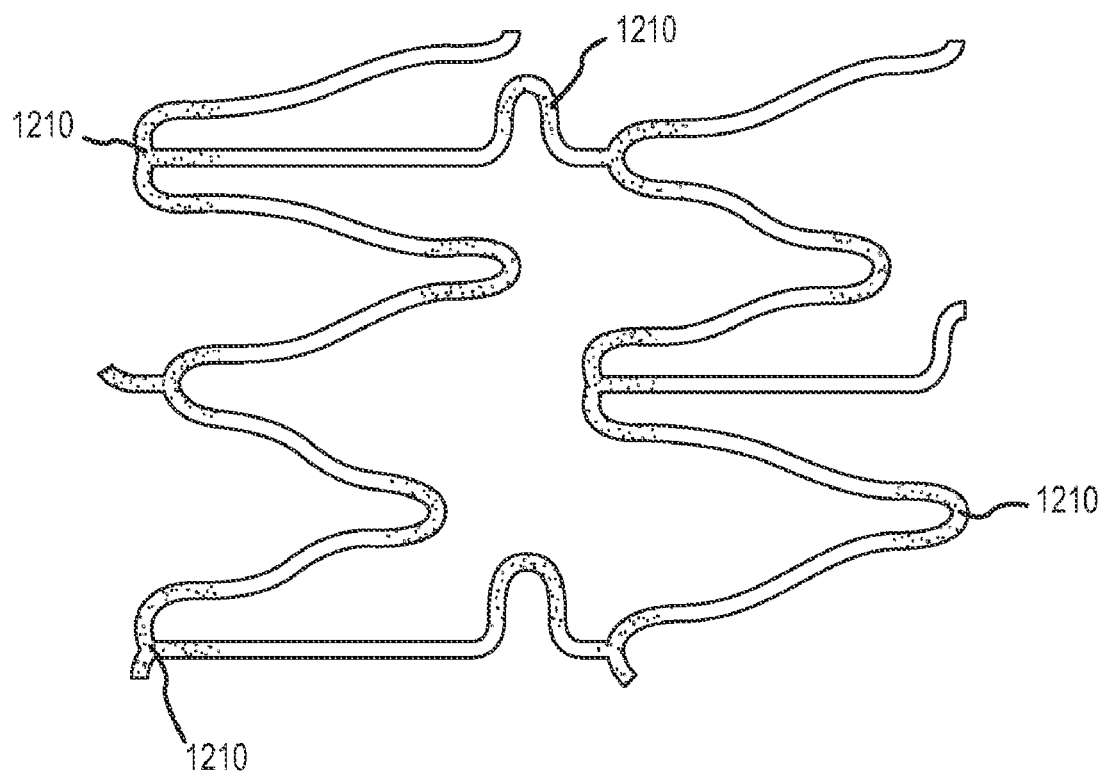
FIG. 12 depicts the location of datum points in an exemplary image according to various aspects of the present invention.
Figure 13:
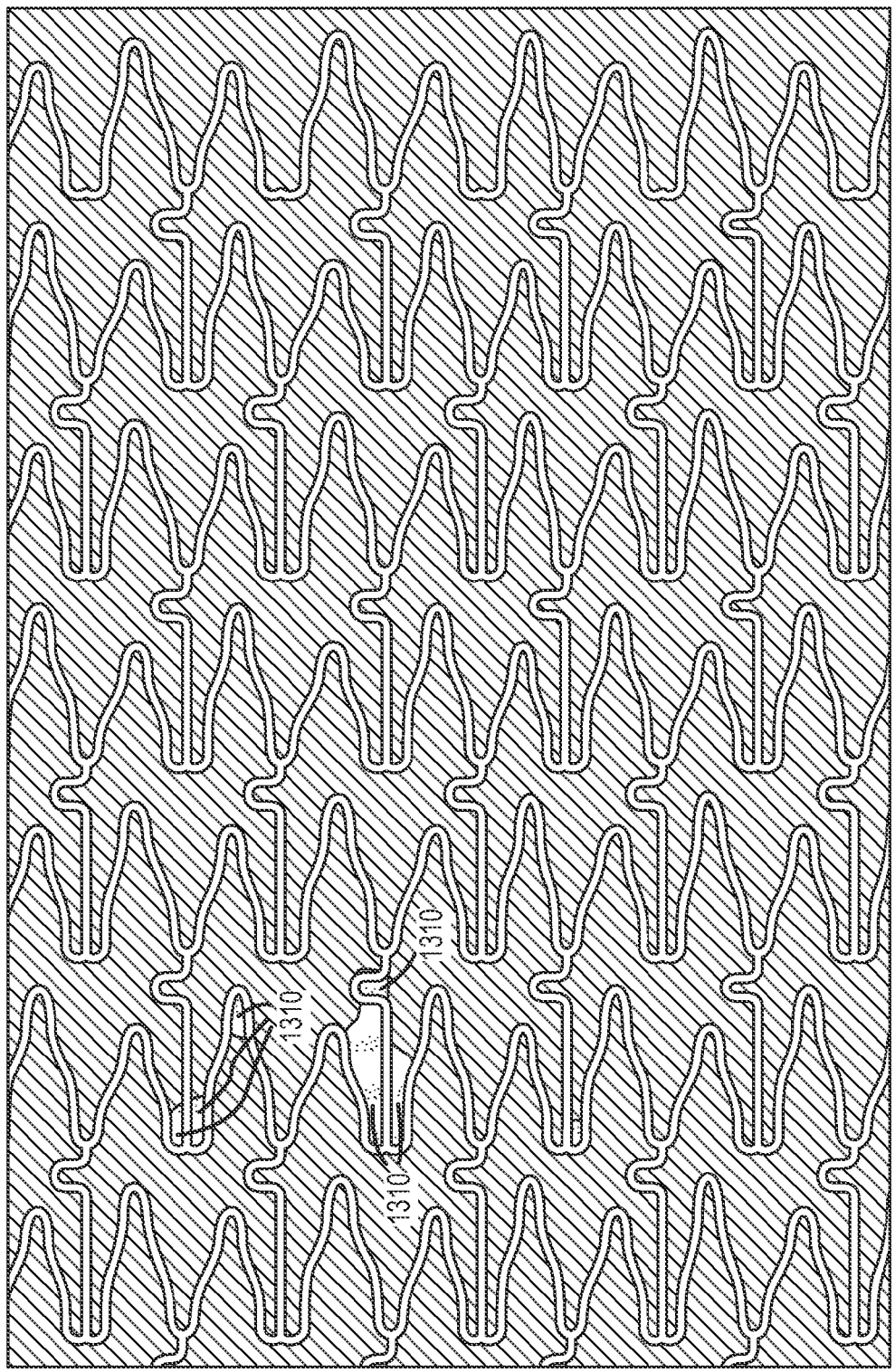
FIG. 13 depicts a two-dimensional image of the structure of a stent, wherein defects are present between the struts of the stent.
Figure 14:
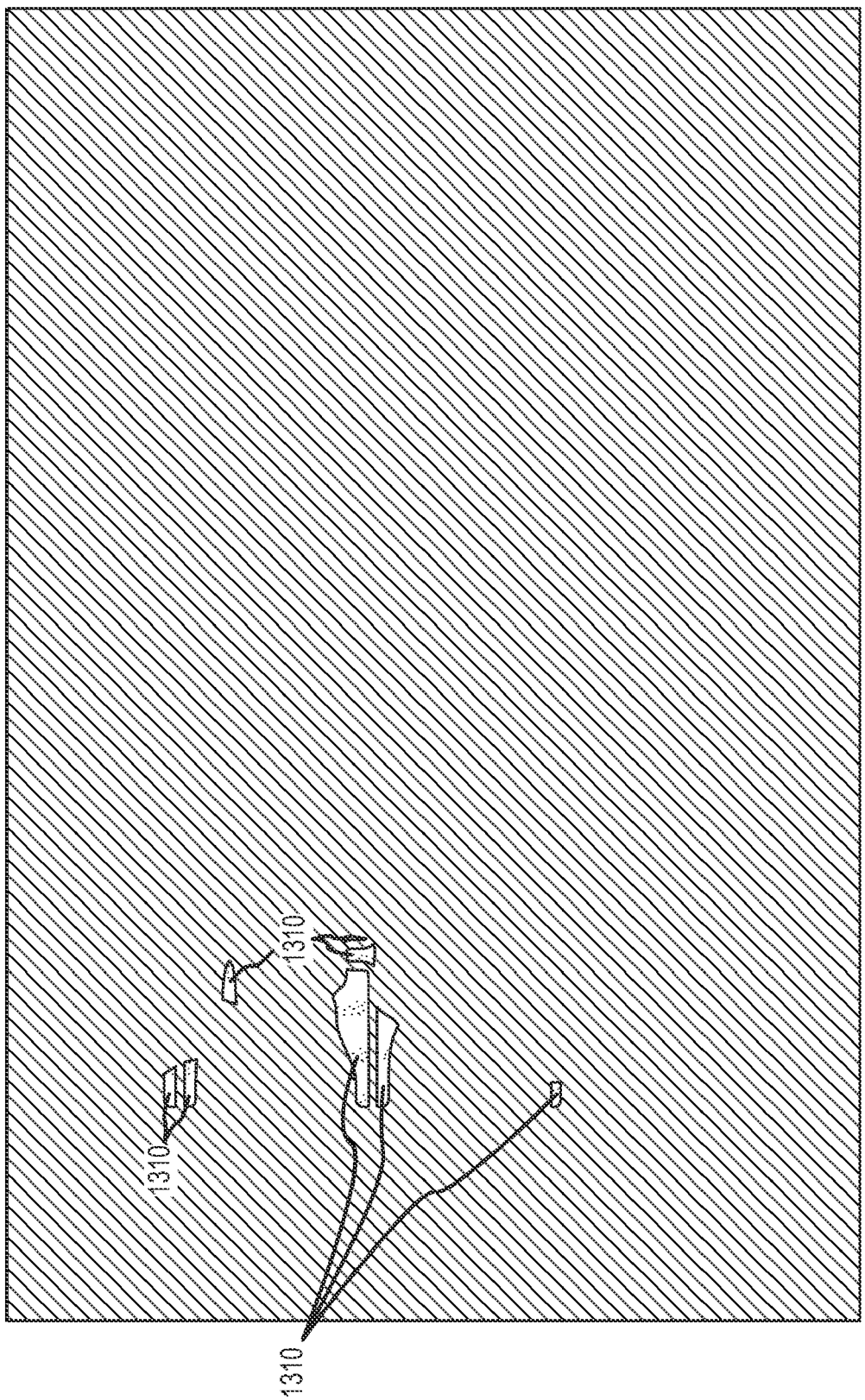
FIG. 14 depicts the two-dimensional image in FIG. 13 wherein the structure of the stent has been subtracted to aid in identifying defects.

The images are analyzed to identify any defects (1080). FIG. 11 depicts an exemplary process for analyzing images for defects (1080) according to various aspects of the present invention. Datum points corresponding to the structure of the stent 200 are located in the image (1110). The datum points correspond to any element of the stent 200 that may be used to identify the general structure of the stent 200, and may be selected according to any criteria. For example, referring to FIG. 12, the shaded portions of the struts 210 indicate datum points 1210 that are selected to correspond the beginning and ending points of struts 210 in the stent 200. The datum points are used to determine the proper width of struts 210 in the image (1120). Defects are determined by identifying deviations in the measured width of individual struts 210 in the image (1130). Any other suitable dimension of a feature of a strut 210 may be identified (1120) and analyzed to find defects (1130), such as a strut's 210 height, length, etc. For example, defect analysis (1130) may be performed on a stent 200 to detect any distortion that might have occurred during the manufacturing process. Additionally, defects lying between the struts 210 in a stent 200 may be identified by masking the image of the struts 210 (1140) and analyzing the remaining features in the image to determine whether they are defects in the stent 200 (1150). FIG. 13, for example, depicts a representative image of a stent 200 prior to masking. In this image, the struts 210 forming the stent 200 are represented in two-dimensions by a light structure on a dark background. Defects 1310 between the struts 210 of the stent 200 show up as light shading. In order to aid in identifying the defects 1310, referring now to FIG. 14, the structure of the stent 200 is masked out, leaving the light-shaded defects 1310 in the image. The structure of the stent 200 may be masked out of an image in any suitable manner. For example, software running on a computer system may identify the structure of the stent 200 in a digitized image, and remove and/or fill that structure to match the background of the image.

Any type of defect may be identified by the process for analyzing images (1080), such as defects associated with the manufacture of a stent 200, or defects associated with a coating covering the stent 200. Defects associated with any suitable coating may be detected, such as a polymer coating, a drug coating, a combination of a drug and polymer coating, and/or any other form of coating. An analysis process may be performed using any number of images. For example, an inspection system 100 may analyze single images of portions of a cylinder after each image is created, or process multiple images together. Any portion of a process for inspecting cylinders may be performed manually by a human being or automatically, such as by using software operating on a computer system.

Figure 15:
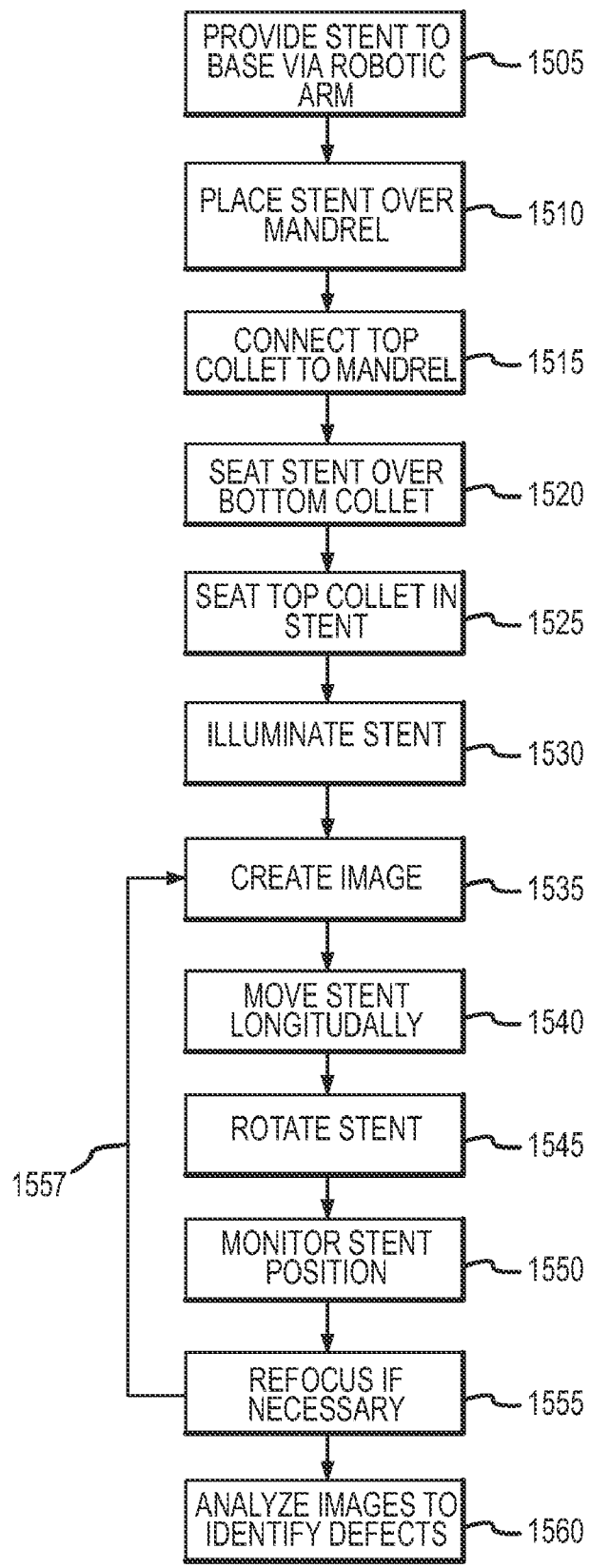
FIG. 15 is a process flow diagram illustrating an exemplary process for inspecting a stent according to various aspects of the present invention.

FIG. 15 illustrates another exemplary inspection process that may be employed by an inspection system 100 according to various aspects of the present invention. A stent 200 is automatically provided to a base 510 by a transfer arm 710 (1505). The stent 200 is placed over a mandrel 610 connected to a bottom collet 620 (1510). A wire capture arm 640 brings a top collet 630 in connection with the mandrel 610 (1515). A stabilizer arm 650 grasps the stent 200, then lifts and releases the stent 200 to cause it to settle over a conical surface on the bottom collet 620 (1520). When properly settled, the interior of the stent 200 engages the conical surface of the bottom collet 620 without the stent 200 touching the mandrel 610. The stabilizer arm 650 interfaces with the top collet 630, lifting and dropping the top collet 630 to cause a conical surface on the top collet 630 to settle into the interior of the stent 200 (1525).

With the stent 200 engaged by the top and bottom collets 620, 630, the stent 200 is positioned between two light sources 130 and two cameras 140, 520, 530, where each light source 130 illuminates the stent 200 from behind each camera 520, 530 (1530). The inspection camera 520 creates an image of the stent 200 that includes the full width of the stent 200 and features protruding from the edges of the stent 200 (1535). The base 510 moves up and down to allow the inspection camera 520 to create images along the full length of the stent 200 (1540). The base 510 rotates the stent 200 a certain amount, such as 5 degrees, to expose a new portion of the stent 200 to the inspection camera 520 (1545). The focus feedback camera 530 monitors whether the stent 200 changes position on the mandrel 610 at any point during the imaging process (1550). If a change in position is detected, the inspection camera 520 is refocused accordingly (1555). The inspection camera 520 may be refocused in any suitable manner, such as by adjusting a focus control in the camera 520, physically moving the camera with relation to the stent 200, and the like. The process may be repeated (1557) in order to capture images of the full diameter of the stent 200. Since both edges of the stent 200 are being captured in a single image, the stent 200 need only be rotated 180 degrees to image the full diameter of the stent 200.

Figure 16:
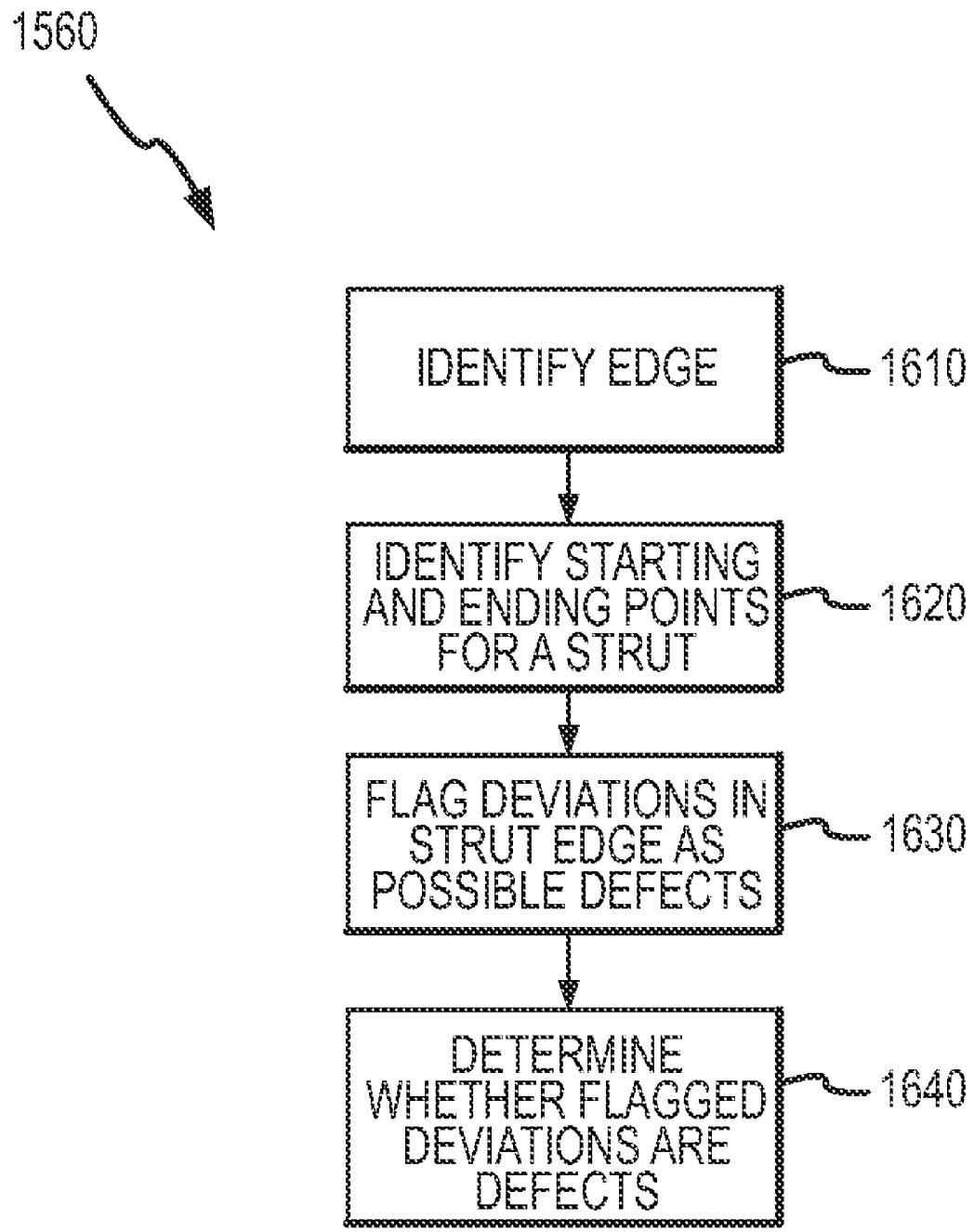
FIG. 16 is a process flow diagram illustrating an exemplary process for identifying defects associated with a stent according to various aspects of the present invention.
Figure 17:
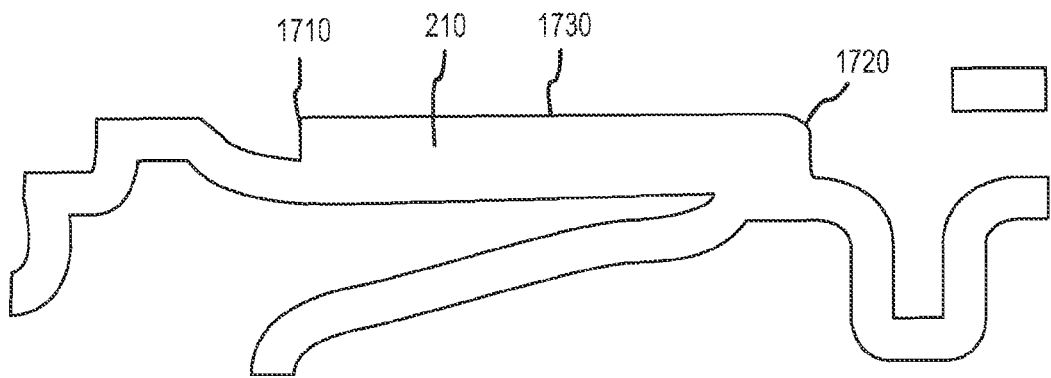
FIGS. 17, 18, 19, and 20 are exemplary images of portions of a stent that illustrate elements of the process described in FIG. 16.
Figure 18:
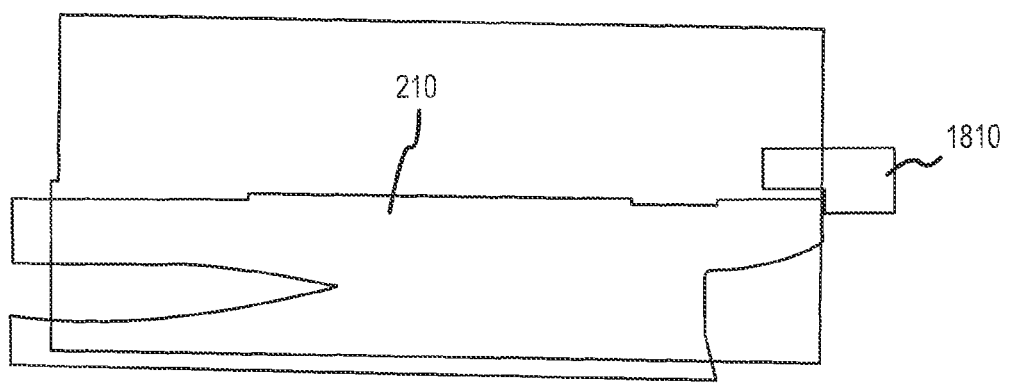
Figure 19:
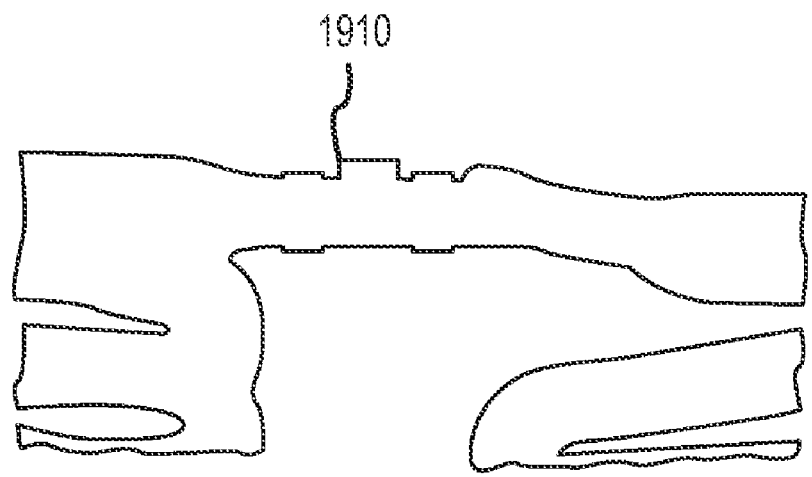
Figure 20:
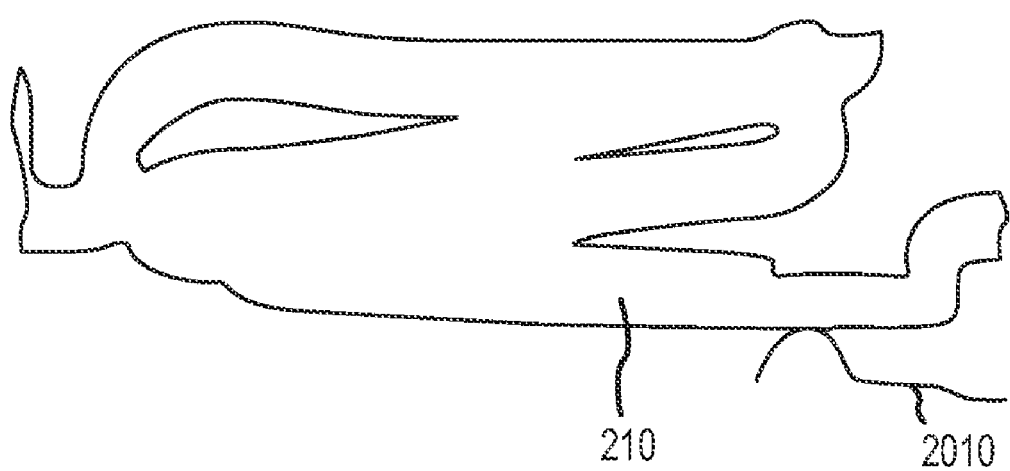

The images are analyzed to identify defects protruding from the stent 200 (1560). An exemplary process for analyzing an image for protruding defects (1560) is illustrated in FIG. 16. An approximate edge location is identified from the image (1610). For each strut 210 comprising a portion of the edge, referring now to FIG. 17, a starting position 1710 and an ending position 1720 of the strut is identified (1620). The line 1730 between the starting position 1710 and ending position 1720 defining the edge of the strut 210 is analyzed and any deviations from the line 1730 that are outside defined tolerances (i.e. height, length, and area) are flagged as potential defects (1630). For each deviation flagged as a potential defect, a determination is made as to whether the deviation is part of the structure of the stent 200 (1640). For example, a deviation found near the edge of the strut may be analyzed to determine the relative size of the deviation compared to other features in the image to determine whether it is a defect or part of the structure of the stent 200. Referring to FIG. 18, a non-linear link 1810 partially caught in the scan of the strut 210 can be identified as part of the structure of the stent 200 and is not considered a defect. Similarly, referring now to FIG. 19, a deviation caused by a non-linear link configuration 1910 having a substantially uniform thickness at the deviation as well as on either end of the deviation may be identified as part of the structure of the stent 200 as opposed to a defect. However, as shown in FIG. 20, a deviation 2010 that has a thickness less than the minimum normal strut 210 thickness can be identified as a defect. The process for defect analysis (1560) may be repeated for each strut in an image. A process for defect analysis (1560) may be performed for any number of images and for some or all of the edges of a stent 200 captured in an image.

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Furthermore, the connecting lines shown in the various figures are intended to represent exemplary functional relationships and/or physical couplings between the various elements. Many alternative or additional functional relationships or physical connections may be present in a practical system.

Changes and modifications may be made to the disclosed embodiment without departing from the scope of the present invention. These and other changes or modifications are intended to be included within the scope of the present invention, as expressed in the following claims.

What is claimed is:

1. A method for inspecting a stent, the method comprising:
   creating an image of the stent; and
   analyzing the image, the analyzing comprising masking out a strut of the stent in the image, and identifying a defect associated with a feature remaining in the image after the masking out of the strut.

2. The method of claim 1, wherein the analyzing of the image is performed by a computer system.

3. The method of claim 1, wherein the analyzing of the image comprises:
   locating one or more datum points associated with the strut;
   using the datum point to determine a correct dimension of the strut; and
   identifying a defect associated with a feature having a dimension different from that of the correct dimension of the strut.

4. The method of claim 1, wherein the creating of the image of the stent comprises disposing a background mandrel within the interior of the stent, and illuminating the stent so that the strut and the defect appear relatively bright against a dark background.

5. The method of claim 1, wherein the stent comprises a coating and the analyzing of the image to inspect the stent for defects includes identifying defects associated with the coating.

6. The method of claim 1, further comprising:
   rotating the stent; and
   detecting a shift in position of the stent during the rotation which causes the stent to be out of focus on an inspection camera for creating the image of the stent, the detecting of the shift in position performed using an other camera.

7. A system for inspecting a stent, the system comprising:
   a camera for creating an image of the stent; and
   a computer system for controlling the camera, the computer system configured to mask out of the image a strut of the stent and to identify a defect associated with a feature remaining in the image after the strut is masked out.

8. The system of claim 7, further comprising an other camera interfacing with the computer system, the computer system configured to cause the camera for creating the image to refocus on the stent based on an image from the other camera.

9. The system of claim 7, wherein the computer system is configured to:
   locate one or more datum points associated with the strut;
   use the datum point to determine a correct dimension of the strut; and
   identify a defect associated with a feature having a dimension different from that of the correct dimension of the strut.

10. The system of claim 7, further comprising a background mandrel configured to fit within the interior of the stent, and a light source oriented to illuminate the stent so that a plurality of struts of the stent and the defect appear relatively bright against a dark background.

\* \* \* \* \*